US005494826A

United States Patent [19]
Stetter et al.

[11] Patent Number: 5,494,826
[45] Date of Patent: Feb. 27, 1996

[54] MICROCALORIMETER SENSOR FOR THE MEASUREMENT OF HEAT CONTENT OF NATURAL GAS

[75] Inventors: Joseph R. Stetter, Naperville; G. Jorgan Maclay, Maywood, both of Ill.

[73] Assignee: Gas Research Institute, Inc., Chicago, Ill.

[21] Appl. No.: 228,906

[22] Filed: Apr. 18, 1994

[51] Int. Cl.$^6$ ............................................. G01N 25/20
[52] U.S. Cl. .................... 436/147; 73/24.01; 73/25.03; 364/557; 374/37; 422/83; 422/94; 422/95; 422/98
[58] Field of Search ................ 436/147, 2; 73/24.01, 73/25.03; 364/557; 374/37; 422/63, 94, 95, 98

[56] References Cited

U.S. PATENT DOCUMENTS

| | | | |
|---|---|---|---|
| 4,443,791 | 4/1984 | Risgin et al. | 340/634 |
| 4,560,585 | 12/1985 | Khilnani | 427/103 |
| 4,703,646 | 11/1987 | Müller et al. | 73/23 |
| 4,720,421 | 1/1988 | Khilnani | 428/222 |
| 4,854,155 | 8/1989 | Poli | 73/27 R |
| 5,012,432 | 4/1991 | Stetter et al. | 364/557 |
| 5,055,266 | 10/1991 | Stetter et al. | 422/83 |

*Primary Examiner*—Timothy M. McMahon
*Assistant Examiner*—N. Bhat

[57] ABSTRACT

A microcalorimeter includes instrumentation for reducing measurement errors due to system fluctuations. One or more sensors is utilized to detect heat content of a sample gas, and create a composition independent system. Instrumentation for automatically compensating for pressure and temperature variations is also employed in the microcalorimeter. A method for continuously measuring the BTU content of a gas utilizing the microcalorimeter includes steps for adjusting system parameters in response to changes in ambient conditions and sample gas composition to further reduce measurement error.

24 Claims, 3 Drawing Sheets

MICROCALORIMETER SENSOR FOR THE MEASUREMENT OF HEAT CONTENT OF NATURAL GAS

FIELD OF THE INVENTION

This invention relates to an apparatus and method for continuously measuring the BTU content of a gas, and more particularly, to an improved microcalorimeter system having means for reducing the effects of fluctuations in system conditions.

BACKGROUND OF THE INVENTION

Accurate measurement of the BTU content of various hydrocarbon gases is extremely important in a wide variety of applications. The BTU content, or heating value of a gas, also known as its enthalpy, is the heat energy stored by the gas in the chemical bonds that are broken during combustion and the energy can be released as sensible heat associated with its temperature, and prior to combustion as latent heat associated with its state ("BTU" is an abbreviation for British thermal units). Measurement of the BTU content of natural gas is of particular importance in industrial processes, such as glass manufacturing and heat treating. Instruments for measuring BTU content can typically utilize a calorimeter or gas chromatograph or a gas sensor comprising a coil of a fine platinum wire coated with a catalyst, such as alumina, to form a bead. In U.S. Pat. No. 5,012,432 to Stetter, et al., which is herein incorporated by reference, the present inventors demonstrated that the overall dimensions of the sensor's bead are often less than a cubic millimeter.

During operation of the instrument, the sensor is heated by passing current through the platinum wire. When a combustible gas is contacted with the hot catalyst on the bead surface, the typical hydrocarbon gas (HC) reacts to produce heat ($\Delta H$) according following general equation:

$$a[HC]+bO_2 \rightarrow cCO_2+dH_2O+\Delta H \tag{1}$$

where a,b,c,d are constants. The amount of heat produced, $\Delta H$, is determined by the enthalpy for the particular hydrocarbon gas, the degree of combustion, and number of molecules reacting or concentration ([HC]).

The platinum wire in the sensor can also function as a resistance thermometer, that is, its resistance changes with temperature. When the combustible gas reacts at the catalyst surface, the heat produced ($\Delta H$) causes an increase in sensor temperature ($\Delta T$) that can be related to the sensor's heat capacity ($C_p$) and the heat released according to the equation:

$$\Delta T = \propto \Delta H/C_p \tag{2}$$

Where "$\propto$" is the fraction of the released heat, $\Delta H$, that goes into heating the sensor which has heat capacity, $C_p$. The change in sensor temperature, in turn, causes a change in resistance of the sensor's platinum wire. The change in resistance of the wire is monitored by placing the sensor in a Wheatstone bridge circuit with a compensating element (passivated and matched) and two known resistors. Thus, small changes in temperature are detected as an imbalance in the resistance bridge circuit. This relationship is usually expressed according to the following equation:

$$V = K \times [HC] \tag{3}$$

where V is the signal from the sensor corresponding to the imbalance in the bridge in volts. When the sensor is operated under constant conditions, V is dependent only upon the relative amount, or concentration of the hydrocarbon gas in the sample as illustrated in equation (3). K is an instrument constant obtained through calibration of the sensor with a known concentration of a gas in air and varies with the type of gas being detected and the combustion conditions.

A microcalorimeter utilizing the above-described technology to measure the heat content of natural gas is disclosed in U.S. Pat. No. 5,012,432. A microcalorimeter is a computer-controlled instrument which samples a fixed number of moles of sample gas. The Stetter et al. microcalorimeter offers convenient portability and a low production cost while retaining high performance, which are features that are not available in many other prior art calorimeters or equivalent BTU measurement devices. However, these positive features of the device are often outweighed by the device's susceptibility to numerous sources of error. In particular, inaccurate output signals used for calculating BTU content may result due to only slight changes in conditions within the sensor chamber. Further, accuracy of the device varies with the composition of the sample gas, and age and composition of the sensor being utilized.

SUMMARY OF THE INVENTION

Thus, it is a purpose of the present invention to overcome the disadvantages of the prior art and thereby provide an apparatus and method for measuring BTU content of a gas which reduce and/or compensate for various inherent inaccuracies in the measurements.

In accordance with a preferred embodiment of the invention, the apparatus comprises at least one catalytic sensor for receiving a gas sample and for producing an output signal related to the BTU content of the gas sample. The apparatus further comprises flow injection means for measuring out a precise predetermined amount of the sample gas and for diluting the sample gas with a carrier gas, and signal processing means connected to the sensor for receiving signals and for calculating the BTU content of the sample gas based on the signal.

Preferably, the apparatus comprises at least two catalytic sensors having different compositions and characteristics. Alternatively, the two sensors have the same composition and characteristics, but are operated at one or more different conditions of temperature, pressure, dilution, composition, geometry and flow rate; thereby providing a composition independent signal.

The invention is further directed to a method of measuring the BTU content of a gas using a catalytic sensor positioned in a combustion chamber. According to the method, a current is applied to the sensor filament to heat the sensor to its operating temperature. The sensor is then calibrated by passing a first calibration gas over the sensor to obtain a first output signal, and then passing a second calibration gas with the same heat content over the sensor to obtain a second output signal. The first and second signals are then compared and the temperature of the sensor is adjusted. These steps are repeated until the two signals are approximately equal. The sensor is then contacted with the sample gas to oxidize or combust the gas and the temperature and resistance changes in the sensor are monitored. The current to the filament is adjusted based on the changes to maintain a constant sensor temperature or resistance during the oxidation. During adjustment of the current, the voltage change across the sensor is measured. The BTU content is calculated from this measured voltage change.

In yet another preferred method of the invention, a current is applied to the filament to heat the sensor to an operating temperature. The sensor is calibrated by passing a gas having a known BTU content over the sensor to obtain a standard for measurement of the BTU content of a sample gas. The sensor is then contacted with the sample gas to oxidize or combust the gas and temperature or resistance changes in the sensor are monitored and the current to the filament is adjusted based on the changes to maintain a constant sensor temperature (in other words, keep the sensor's resistance constant) during the oxidation. BTU content of the sample gas is calculated based on the ratio of the signal for the known BTU value of the standard gas when compared to the sample gas output signals. In addition, ambient temperature and pressure changes in the sensor chamber are monitored during the step of reducing the voltage. A correction factor based on the ambient temperature and pressure changes is calculated and multiplied by the calculated BTU content to calculate the actual BTU content of the sample gas.

It is, therefore, an object of the invention to provide a microcalorimeter which provides a composition independent output signal for use in measuring the BTU content of a gas.

It is another object of the invention to provide a microcalorimeter having a constant temperature circuit and including means for automatically compensating for changes to the sensor which may occur under ambient conditions.

It is yet another object of the invention to provide a method for measuring BTU content of a gas using a microcalorimeter in which more than one calibration gas is utilized to provide a composition independent output signal.

It is still another object of the invention to provide a method for measuring BTU content of gas which compensates for ambient temperature and pressure changes in the sensor chamber.

These and other objects of the present invention will become apparent from the detailed description to follow.

DESCRIPTION OF THE PREFERRED EMBODIMENTS

Figure 1:
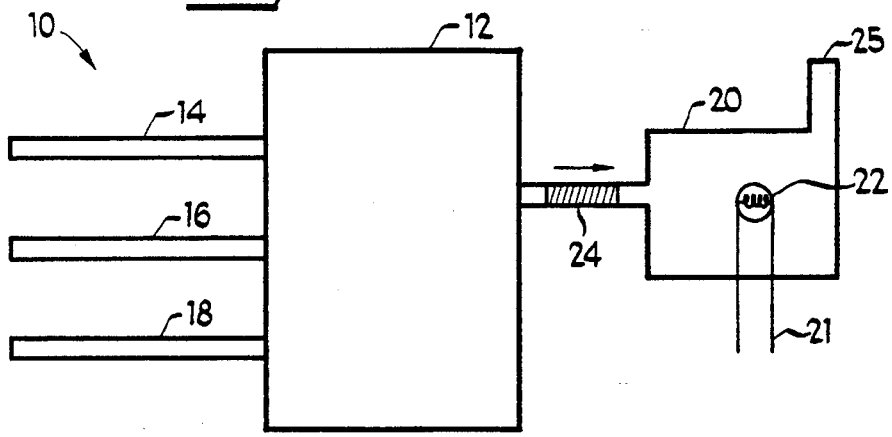
FIG. 1 is a schematic block diagram of the microcalorimeter of the invention.

Referring now to the drawings and, more particularly to FIG. 1, a schematic block diagram of the microcalorimeter 10 of the present invention is shown. The microcalorimeter 10 comprises a computer-controlled flow injection system 12 into which gases are injected and prepared for analysis. The microcalorimeter further comprises a combustion chamber 20 wherein the prepared gas samples are passed over a sensor 22 to oxidize the gas samples and to generate the analytical signal. Signal processing means (not shown) is connected to the sensor output 21 for receiving the output signal and calculating the BTU content of the sample gas.

After the gas is oxidized it is vented to the atmosphere through a vent 25 in the combustion chamber 20. The combustion chamber 20 is typically fabricated from a ceramic or aluminum material.

In operation, a calibration gas 18 of known heat content or a sample gas 14 of unknown heat content is injected into the instrument 12, where it is diluted with a carrier gas 16, typically air, prior to contact with the sensor 22 which has been heated to its operation temperature. The flow injection system 12 introduces a precise predetermined amount of the sample gas or calibration gas into the carrier gas stream. The resultant diluted sample 24 then enters the combustion chamber 20 in the form of a fixed volume gas plug which is passed over the heated sensor 22 where it is catalytically oxidized. The oxidation reaction produces heat, causing a change in the temperature of the sensor 22. The temperature change is directly proportional to the heat released ($\Delta H$) and is used to determine the heat content of the gas sample.

Figure 2:
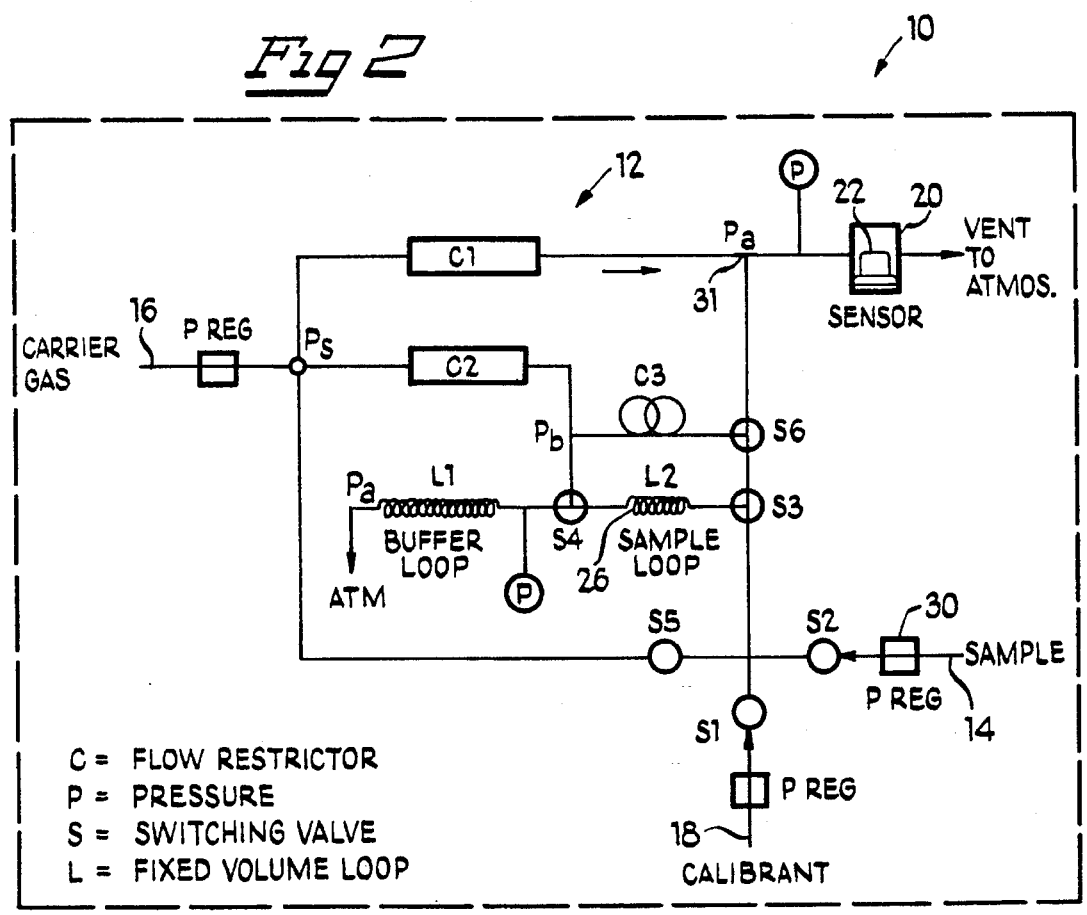
FIG. 2 is a pneumatic diagram of the microcalorimeter.

FIG. 2 shows a pneumatic diagram of the microcalorimeter 10 of the present invention. The pneumatic system provides the constant volume gas samples 24 at known pressures and temperatures (i.e., known number of molecules) and the proper sequencing of all operations. The microcalorimeter 10 operates in a three-step cycle. First, a fixed flow rate of the carrier gas 16 is passed over the sensor 22 to obtain a zero reading. Second, a fixed number of moles of sample at known pressure and temperature of the calibration gas 18 having a known BTU content, is diluted or mixed into the carrier gas 16, passed over the sensor 22 and the sensor's output signal measured. The fixed moles of sample is obtained by introducing the calibration gas 18 at a measured temperature and pressure into a sample loop 26 having a known fixed volume. Finally, a fixed amount of the unknown sample gas 14 is introduced into the sample loop 26 through a pressure regulator 30, diluted with the carrier gas 16 at the mixing tee 31, and passed over the sensor 22.

The output signal produced by the microcalorimeter is graphically represented in terms of millivolts versus time. When only the carrier gas 16 flows by the sensor 22, the output signal is a straight, horizontal baseline. By contrast, when a sample gas 14 or calibration gas 18 are introduced into the sensor chamber 20, the output signal is an excursion peak, the height of which is measured from the baseline. One source of inaccurate measurements results from baseline drift due to system disturbances caused by pressure fluctuation. These disturbances typically result when a sample gas or calibration gas is introduced into the carrier gas stream. To reduce these system disturbances, the sample loop 26 is allowed to equilibrate to atmospheric pressure prior to dilution with the carrier gas 16. This procedure reduces temperal fluctuations in the baseline when the sample gas is injected into the flow path of the carrier gas stream. Alternatively, the sample loop 26 may be adjusted to a constant pressure, independent of the ambient pressure, prior to dilution with the carrier gas 18. Still another alternative to eliminating baseline drift is to incorporate an internal calibration gas in the instrument which is automatically analyzed on a periodic basis and/or install an absolute pressure gauge for periodically monitoring ambient pressure. Both of these measurements provide a basis for calculating a correction factor to compensate for ambient pressure fluctuations.

If the carrier gas 16 is atmospheric air and the highest accuracy is required, it is preferable to first draw the carrier gas 16 through a filter to remove impurities, moisture, $CO_2$, and all combustible gases such as CO and hydrocarbons. A small filter may also be employed on the calibration gas 18 and sample gas 14 inlets for removing sulfur gases and other contaminants which can potentially poison or otherwise interfere with the sensor operation. Any filter should be of a type which will only remove gases which are present in small concentrations, the removal of which will not alter measured heat content. The output signal from the sensor is then compared to the output signal for the calibration gas and the BTU content is calculated from the resultant ratio.

For the highest accuracy, the calibration gas 18 may be any gas which is close in composition to the sample gas 14. In certain applications it may be desirable to obtain a calibration that is independent of the gas composition for two different gases. In this case, more than one calibration gas may be utilized. In this embodiment, one of the calibration gases is first passed over the sensor 22 and the sensor output 21 is measured. The second calibration gas is then passed over the sensor 22 and the sensor output 21 is measured. If the response for each gas differs, the temperature of the sensor is then adjusted by altering the sensor voltage. These steps are repeated until essentially the same response per BTU is obtained for both calibration gases, thereby essentially eliminating composition dependence.

Figure 3:
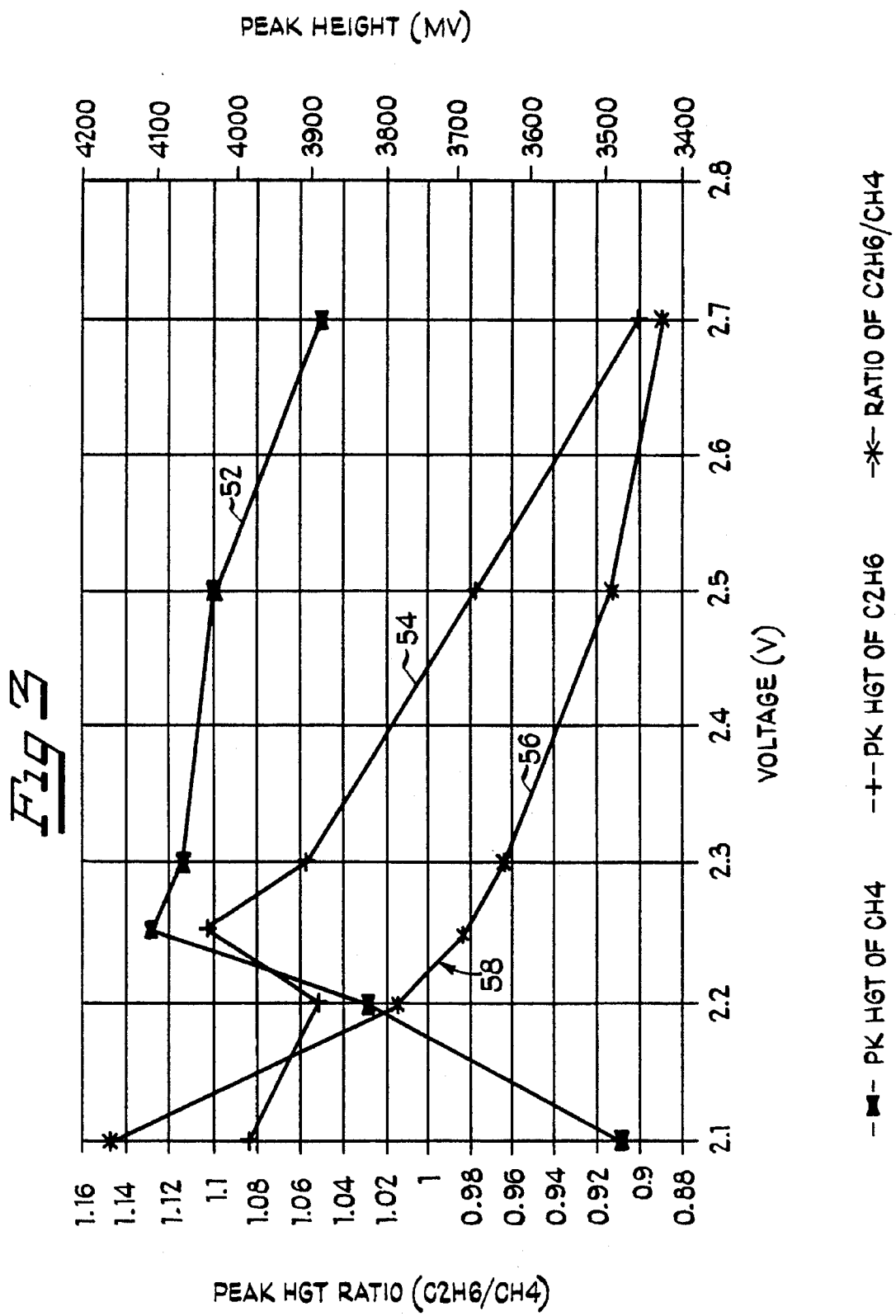
FIG. 3 are sample calibration curves used in optimizing sensor voltage.

FIG. 3 shows sample calibration curves used in optimizing the sensor response for mixtures of methane and ethane. The calibration curves 52, 54 were developed by passing methane and ethane, respectively, over the sensor 22 and plotting output voltage (peak heights in millivolts) versus sensor voltage for six different sensor voltages. Calibration using both of these gases is particularly advantageous when analyzing natural gas of which methane and ethane account for 95% of the total heat content. A third curve 56 represents a ratio of ethane to methane output voltages. Optimum sensor voltage is the voltage at which the ratio is 1.0 or, alternatively, the voltage at which the calibration curves 52, 54 intersect. In the example shown, optimum sensor heater voltage 58 is approximately 2.23 volts. The entire calibration procedure, which may be performed in less than five minutes when utilizing computer software for calculation of optimum sensor voltage, has been found to dramatically reduce the error in microcalorimeter output which is associated with composition dependence.

The sensor 22 is comprised of a platinum filament heater, whose resistance increases monotonically with temperature, and is coated with a catalyst, such as a noble metal catalyst. The sensor 22 is preferably fabricated in a spherical shape to eliminate orientation sensitivity, although a more traditional cylindrical shape is also acceptable. The filament is preferably wound in a uniform coil using a filament winder.

During operation of the microcalorimeter 10, the sensor 22 is operated at a constant temperature to eliminate errors due to temperature dependent parameters. These temperature dependent parameters include thermal conductivity, heat capacity, diffusion coefficients, radiation and convective heat losses. Operation of the sensor 22 at a constant temperature also reduces thermal stresses that age the sensor 22 and degrade performance. Further, operation at a constant temperature has been found to improve short term instrument precision and provide a more stable baseline measurement of the microcalorimeter output signal.

Figure 4:
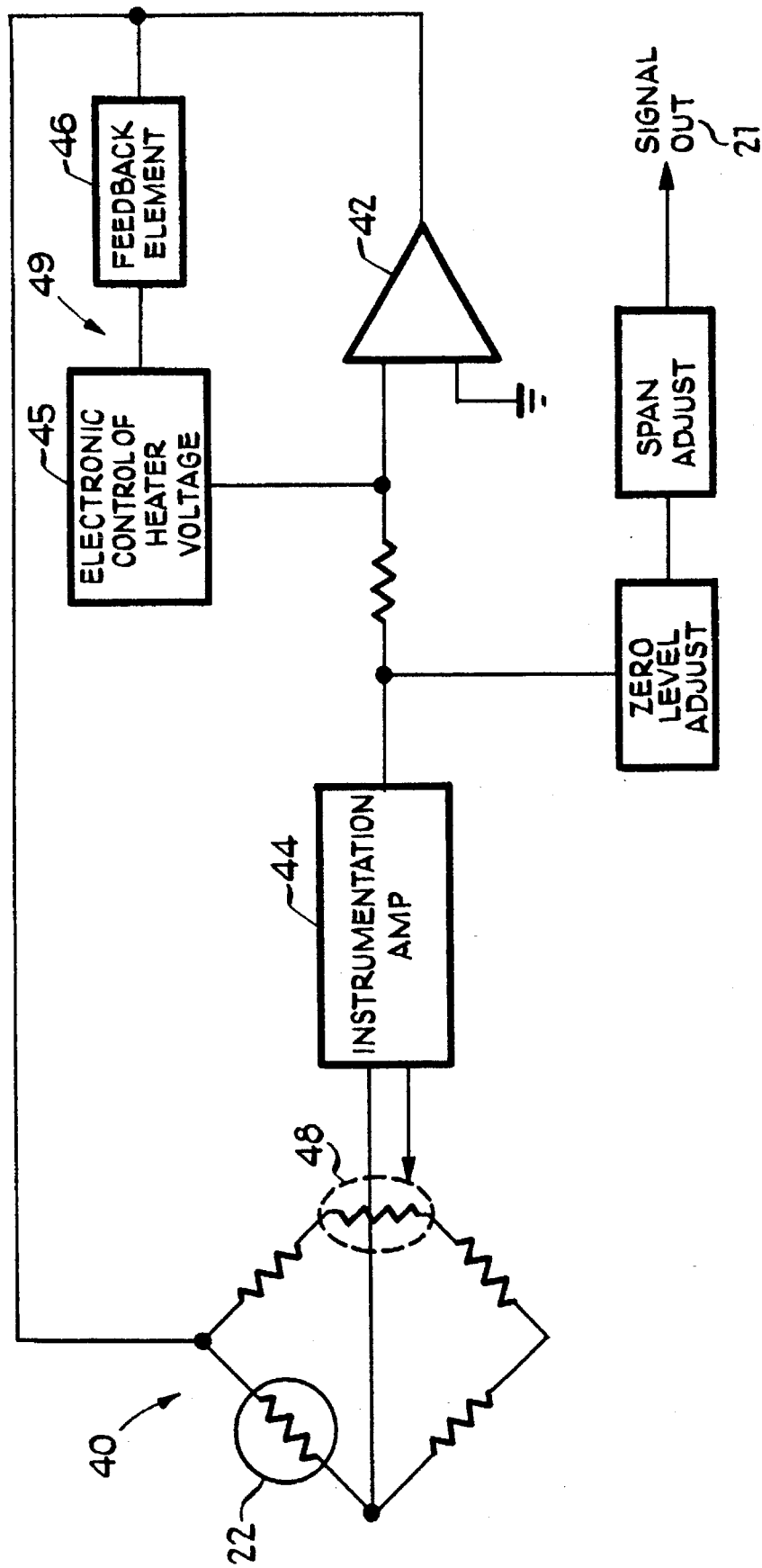
FIG. 4 is a temperature control circuit for the microcalorimeter.

FIG. 4 shows a temperature control circuit for the microcalorimeter 10. The sensor 22 is used as an element in a modified Wheatstone bridge circuit configuration 40. Using this control circuit, noise at the signal peak has been reduced to 0.1% or less of the signal.

During operation, the sensor 22 is heated to its operating temperature and voltage by applying current to the filament by means of an electronic heater voltage controller 45. The bridge 40 is balanced at the resistance of the sensor 22 at its operating temperature using an electrically adjustable potentiometer 48. When a gas is passed over the sensor 22, the reaction of the gas at the catalyst surface causes a change in the temperature and thereby, the resistance of the heater wire in the sensor 22 which, in turn, causes the bridge 40 to go out of balance. The changes in temperature or resistance are measured and output as a signal to the input of an instrumentation op-amp 44, which drives a power op-amp 42 that supplies power to the sensor 22. Power to the sensor 22 is altered until the bridge 40 comes back into balance, i.e., power is altered until the sensor 22 is adjusted to its initial operating temperature. The sensor output signal 47 is the voltage change across the sensor which results when current is applied to maintain the constant temperature or resistance. In order to calculate heat content, the analog temperature signals, i.e., the voltage changes, of the sample and calibration gases are first converted to digital responses which are then compared. The resultant signal ratio and the known heat value of the calibration gas are then used to calculate the heat content of the unknown sample gas 14 in accordance with the formulas disclosed in U.S. Pat. No. 5,012,432.

A complete analysis of the sample and calibrant gases may typically be completed in approximately five minutes. In a preferred method of operation, the microcalorimeter 10 is provided with two continuous loops through which the carrier gas 16 and the sample gas 14 flow. Thus, the sample loop 26 is filled with sample gas or calibration gas while the carrier gas 16 is passing over the sensor 22 during the first step of the process.

Because sensor calibration is performed at a specific ambient temperature and pressure, accuracy of the sensor is further improved by reducing the effect of fluctuations in ambient conditions. Thus, the microcalorimeter may include temperature and/or pressure sensors which measure ambient conditions. When changing ambient conditions are detected, computer software is utilized to calculate a correction factor which is then multiplied by the sensor output signal. Computer logic for calculating a correction factor may be developed through experimental techniques known in the art or, alternatively, commercially available computer software may be purchased and modified as necessary. Alternatively, the critical elements of the microcalorimeter, such as the sensor and bridge, sample gas and calibration loops, and op-amps in the feedback loop may be housed in a thermally-insulated, temperature-controlled box to reduce fluctuations in ambient conditions.

Referring again to FIG. 4, the microcalorimeter further includes an autobalancing circuit 49 which automatically balances the bridge 40 to adjust for changes in the sensor 22 which occur under ambient conditions, i.e., when sample gases are not being analyzed, and cause bridge imbalances. Such changes may, for example, result from typical wear and tear on the sensor which occurs over time and causes the resistance to change and the bridge 40 to go out of balance. The autobalancing circuit 49 also facilitates sensor replacement since individual sensors may have slightly different resistances. When the autobalancing circuit 49 is activated, feedback element 46 receives an output signal from the sensor 22. The signal is compared to the output voltage reference, or set point. If there is a discrepancy, current supplied to the filament is adjusted by means of the heater controller 45 to compensate for change in sensor resistance. The autobalancing circuit 49 can be manually activated or automatically activated on a periodic basis.

In yet another preferred embodiment of the invention, two or more sensors of different composition and characteristics are utilized, such as by positioning them in parallel after mixing tee 31, to enhance microcalorimeter performance. For measurements of the BTU content of natural gas, for example, the microcalorimeter 10 may include a first sensor which is more sensitive to higher molecular weight hydrocarbons and a second sensor which is more sensitive to methane and ethane. Alternatively, two sensors of the same type may be employed, the sensors being operated under different conditions such as different temperatures, flow rates, pressures, dilutions, compositions or geometries. The use of two such sensors provide an improved composition independent signal. The first sensor can be tuned to be independent of light hydrocarbon differences while the second can be optimized for heavy hydrocarbon signals. Of course, there are many ways to construct this experiment which would be obvious to those skilled in the art.

The microcalorimeter of the present invention was tested for both precision, that is, short term repeatability, and long term accuracy utilizing a prototype device. The prototype was designed with a sample loop having a volume of 2 cubic centimeters. Calibration, sample and carrier gases were each supplied at a pressure of about 0.3 bar above atmospheric pressure, or 5 pounds per square inch, to the sensor. Miniature solenoid valves (5 centimeters (cm)×1.4 cm×1.4 cm) were used to switch the carrier gas flow to sweep the fixed volume of sample and calibration gases into the combustion chamber with an air to sample dilution that was held precisely constant and was approximately 30:1. Gas flow to the combustion chamber was further controlled by porous metal disc restrictors to provide flow stability. The sensor was comprised of a platinum filament, coated with layers of alumina and noble metal catalyst on alumina and was about 2 millimeters in diameter. The sensor was operated at a temperature of about 670° C. A 14 bit analog to digital computer was utilized to convert the 0–5 V sensor signals. Testing for precision included repeatedly measuring the heat content of the same composition gas samples. The resulting precision was about 0.2%. The accuracy of the microcalorimeter was determined by taking an average of 5 successive measurements in which the sensor response to the sample gas was compared to the sensor response for methane. A series of these tests was conducted over a 50 day period and demonstrated a long term accuracy for the system of better than 0.5%. The average absolute error for all measured samples was 0.3%. During this 50 day period, recalibration was not repeated, although the voltage on the sensor was changed to maintain approximately the same size signal. This demonstrated that it is unnecessary to run calibration gas prior to each sample gas measurement in order to obtain the desired accuracy. Thus, if the microcalorimeter is used solely for measurements of natural gas, it is only necessary to run the carrier and/or calibration gases once a week or perhaps at less frequent intervals depending upon the accuracy required by the application. This greatly reduces the time required for a measurement, thereby enhancing the speed of operation.

Although the invention has been described in considerable detail with respect to preferred embodiments thereof, variations and modifications will be apparent to those skilled in the art without departing from the spirit and scope of the invention as set forth in the claims.

We claim:

1. A microcalorimeter for measuring BTU content of a gas sample, said microcalorimeter comprising:

flow injection means for measuring out a precise predetermined amount of sample gas and for diluting the sample gas with a carrier gas;

at least two catalytic sensors positioned on an outlet side of said flow injection means for receiving the sample gas and the carrier gas and for producing output signals related to the BTU content of the sample gas, said sensors having substantially identical physical, chemical and electrical properties;

means for simultaneously operating one of said sensors under a first gas exposure condition and a second of said sensors under a different gas exposure condition; and signal processing means connected to outputs of said sensors for receiving said signals and for calculating the BTU content of said sample gas based on said signals.

2. The microcalorimeter according to claim 1 further comprising filter means positioned at an inlet to said flow injection means for removing impurities from said carrier and sample gases.

3. The microcalorimeter according to claim 1 wherein each of said sensors comprises an element of a respective wheatstone bridge circuit configuration, said bridge configurations being balanced at operating temperatures of respective sensors.

4. The microcalorimeter according to claim 3 further comprising a circuit for automatically balancing said Wheatstone bridge circuits.

5. The microcalorimeter according to claim 1 wherein said flow injection means comprises a constant volume sample loop.

6. The microcalorimeter according to claim 5 further comprising means for adjusting or measuring pressure of a gas in said constant volume sample loop.

7. The microcalorimeter according to claim 5 further comprising a second sample loop for measuring a precise predetermined amount of a calibration gas for calibrating said microcalorimeter.

8. The microcalorimeter according to claim 1 wherein said means for operating comprises thermally-insulated boxes for separately housing each of said sensors and for simultaneously operating said sensors under different gas temperatures, pressures, flow rates or dilutions.

9. A microcalorimeter for measuring BTU content of a gas sample, said microcalorimeter comprising:

flow injection means for measuring out a precise predetermined amount of a sample gas and for diluting the sample gas with a carrier gas;

at least two catalytic sensors positioned on an outlet side of said flow injection means for receiving the sample gas and the carrier gas and for producing output signals related to the BTU content of the sample gas, said sensors differing in at least one chemical or physical property for producing different signals in response to the sample gas; and signal processing means connected to outputs of said sensors for receiving said signals and for calculating the BTU content of said sample gas based on said signals.

10. The microcalorimeter according to claim 9 wherein said at least one different chemical or physical property is selected from the group consisting of size, geometry and composition.

11. The microcalorimeter according to claim 9 wherein at least a first of said sensors is more sensitive to high molecular weight hydrocarbons and at least a second of said sensors is more sensitive to low molecular weight hydrocarbons.

12. The microcalorimeter according to claim 11 wherein the second of said sensors is more sensitive to methane and ethane.

13. The microcalorimeter according to claim 9 further comprising filter means positioned at an inlet to said flow injection means for removing impurities from said carrier and sample gases.

14. The microcalorimeter according to claim 9 wherein each of said sensors comprises an element a respective Wheatstone bridge circuit configuration, said bridge configurations being balanced at operating temperatures of respective sensors.

15. The microcalorimeter according to claim 14 further comprising a circuit for automatically balancing said Wheatstone bridge circuits.

16. The microcalorimeter according to claim 14 further comprising thermally-insulated, temperature-controlled boxes for housing each of said sensors and maintaining said sensors under ambient conditions.

17. The microcalorimeter according to claim 9 wherein said flow injection means comprises a constant volume sample loop.

18. The microcalorimeter according to claim 17 further comprising means for adjusting or measuring pressure of a gas in said constant volume sample loop.

19. The microcalorimeter according to claim 17 further comprising a second sample loop for measuring a precise predetermined amount of a calibration gas for calibrating said microcalorimeter.

20. A method of measuring BTU content of a gas comprising: providing a microcalorimeter comprising a catalytic sensor positioned in a combustion chamber, said sensor comprising a filament coated with a catalyst;

applying a current to the filament to heat the sensor to an operating temperature;

calibrating said sensor by the steps of
  passing a first calibration gas having a known BTU content over said sensor to obtain a first output signal,
  passing a second calibration gas having a known BTU content over said sensor to obtain a second output signal,
  comparing said first and second output signals,
  adjusting said operating temperature of said sensor and repeating said steps of passing and comparing until said first and second signals per known BTU content of said first and second calibration gases, respectively, are substantially equal;

exposing said sensor to a sample gas to obtain a sensor signal;

monitoring temperature changes or resistance changes in said sensor during the step of exposing;

adjusting the current to said filament based on said temperature changes to maintain a constant sensor temperature or based on said voltage changes to maintain a constant voltage during said step of exposing;

measuring voltage change across said sensor or change in sensor output signal required to maintain the constant sensor temperature or the constant voltage, respectively; and calculating said BTU content of said sample gas from said voltage change or said change in sensor output signal.

21. The method according to claim 20, further comprising the step of diluting said first and second calibration gases with a carrier gas before said step of calibrating and diluting said sample gas with a carrier gas before said step of exposing.

22. The method according to claim 20 further comprising the step of filtering said carrier, sample and calibration gases before said steps of calibrating and exposing said gases to said sensor to remove impurities in said gases.

23. The method according to claim 20 wherein said sample gas comprises natural gas and said first and second calibration gases comprise methane and ethane.

24. A method of measuring BTU content of a gas comprising: providing a microcalorimeter comprising a catalytic sensor positioned in a combustion chamber, said sensor comprising a filament coated with a catalyst;

applying a current to the filament to heat the sensor to an operating temperature;

calibrating said sensor by passing a calibration gas over said sensor to obtain a standard measurement;

contacting said sensor with a sample gas to react said gas and cause a sensor signal;

monitoring temperature or resistance changes in said sensor during the reaction of said gas;

adjusting the current to said filament based on said temperature or resistance changes in said sensor to maintain a constant sensor temperature during said reaction;

measuring voltage change across said sensor during the reaction of said gas;

monitoring ambient temperature and pressure changes in said chamber during said step of adjusting;

calculating a correction factor based on said ambient temperature and pressure changes in said chamber;

calculating a BTU content of said sample gas from said voltage change and said standard measurement; and multiplying said BTU content by said correction factor to calculate actual BTU content of said sample gas.

* * * * *